(12) United States Patent
Mahe et al.

(10) Patent No.: US 6,337,315 B1
(45) Date of Patent: Jan. 8, 2002

(54) ANTI-INFLAMMATORY COMPOSITIONS COMPRISING PEPTIDE DERIVATIVES OF α-MSH/ALGAL EXTRACTS

(75) Inventors: Yann Mahe, Morsang sur Orge; Nelly Billoni, Valmondois; Lionel Breton, Versailles; Lien Bui-Bertrand, Savigny sur Orge, all of (FR)

(73) Assignee: Societe L'Oreal S.A., Paris (FR)

( * ) Notice: Subject to any disclaimer, the term of this patent is extended or adjusted under 35 U.S.C. 154(b) by 0 days.

(21) Appl. No.: 09/353,650

(22) Filed: Jul. 15, 1999

(30) Foreign Application Priority Data

Jul. 15, 1998 (FR) .............................................. 98-09055

(51) Int. Cl.$^7$ ................................................. A01N 37/18
(52) U.S. Cl. .................. 514/2; 514/2; 514/12; 514/14; 514/25; 514/501; 424/435; 424/49; 424/185.1; 530/300; 530/350; 530/324; 530/327; 530/399; 435/69.1; 435/69.7; 435/6; 435/325; 435/374; 435/378
(58) Field of Search ................ 435/325, 69.1, 435/374, 378, 69.7, 6; 424/435, 49, 185.1; 514/2, 12, 501, 14, 25; 530/324, 300, 350, 327, 399

(56) References Cited

U.S. PATENT DOCUMENTS

| | | | |
|---|---|---|---|
| 5,028,592 A | | 7/1991 | Lipton .......................... 514/18 |
| 5,157,023 A | * | 10/1992 | Lipton .......................... 514/18 |
| 5,468,474 A | * | 11/1995 | Honda et al. ............... 424/70.1 |
| 5,767,095 A | * | 6/1998 | Winget ......................... 514/25 |
| 5,830,994 A | * | 11/1998 | D'Hinterland et al. ...... 530/200 |
| 5,879,688 A | * | 3/1999 | Coury et al. ................. 424/401 |

FOREIGN PATENT DOCUMENTS

| | | | |
|---|---|---|---|
| FR | 2733421 | | 10/1996 |
| FR | 2753903 | | 4/1998 |
| WO | 95/08564 | | 3/1995 |
| WO | WO 98/25584 | * | 6/1998 |

* cited by examiner

Primary Examiner—Karen Cochrane Carlson
Assistant Examiner—Hope A. Robinson
(74) Attorney, Agent, or Firm—Burns, Doane, Swecker & Mathis, L.L.P.

(57) ABSTRACT

Anti-inflammatory compositions, well suited for a wide variety of therapeutic/cosmetic applications, comprise combinatory immixture of (1) an effective anti-inflammatory amount of at least one peptide derivative of α-type melanocyte stimulating hormone (α-MSH), or functional biological equivalent thereof, and (2) an effective anti-inflammatory response-enhancing amount of at least one marine algal extract.

19 Claims, No Drawings

ANTI-INFLAMMATORY COMPOSITIONS COMPRISING PEPTIDE DERIVATIVES OF α-MSH/ALGAL EXTRACTS

CROSS-REFERENCE TO PRIORITY APPLICATION

This application claims priority under 35 U.S.C. §119 of FR-98/09055, filed Jul. 15, 1998, assigned to the assignee hereof and hereby expressly incorporated by reference.

BACKGROUND OF THE INVENTION

1. Technical Field of the Invention

The present invention relates to novel compositions comprising an effective anti-inflammatory amount of at least one peptide derivative of α-type melanocyte stimulating hormone (α-MSH), or of any functional biological equivalent thereof, formulated intimately admixed with at least one algal extract of marine origin. This invention also relates to controlling disorders involving an inflammatory process and to cosmetic treatments by administering the subject novel compositions to individuals in need of such treatments.

2. Description of the Prior Art

Inflammation (or the inflammatory process) is a set of biological reactions which exist throughout the animal kingdom. In man, two patients out of three exhibit an inflammatory syndrome. The inflammation may be localized. It may be defined as the first response to any local attack by means of a series of non-specific reactions which are triggered whatever the initial cause and which take place in three consecutive steps: vascular step, cellulovascular step and tissue fibrosis step.

There is a symptomatic gradation of the inflammation, which transforms from the sensation of skin discomfort, of stretching and of itching to swelling, pain, redness and/or heat. These symptoms are generally due to infiltration of the injured tissues with an edema and/or to vasodilatation of the capillaries.

The signs of the inflammation can extend as far as fever, a state of general malaise and/or an increase in the concentration of certain proteins of the blood plasma.

Inflammation is a phenomenon which involves, inter alia, a series of local cell reactions and the release of cytokines and other mediators such as substance P, prostaglandins, leukotrienes, bradykinin, histamine or serotonin.

The inflammation is manifested by a change in blood flow with, at the site which is under attack, an increase in vascular permeability leading to leakage of plasma proteins towards the extracellular fluid as well as an extravasation of blood cells, in particular leucocytes, neutrophils and macrophages, towards the inflammatory site.

These phenomena are in fact the result of the action of inflammation mediators. Factors which are involved in these inflammatory phenomena, and which are representative, are the cytokines, including, in particular, interleukin 1-α, interleukin 1-β and interleukin 6, the α and β tumor necrosis factors (TNF α and TNF β), the chemokines, such as interleukin 8 or the monocyte chemotactic and activating factor (MCAF), or else other chemotactic factors which are responsible for recruiting lymphocytic cells, monocytic cells, Langerhans cells or basephilic cells at the inflammatory site, such as the B-4 leukotrienes, or else other factors involved in the inflammatory cascade, such as arachidonic acid or the prostaglandins, including, in particular, the E2 prostaglandins.

The inflammatory phenomena are associated with a large number of disorders which range from simple skin discomfort to pathological disease states. The following are exemplary: skin disorders such as sensitive skins, skin discomfort, skin stretching, skin itching, skin swelling, skin pain, skin flushing, heat sensation of the skin, erythemas, in particular due to ultraviolet rays, pruritus, erythema nodosum, urticaria, insect bites, allergies, alopecia in its inflammatory phases, articular ailments such as rheumatoid arthritis, osteoarthritis, tendinitis, periarthritis, spondylarthropathies or the articular impairments of the chronic enteropathies, rheumatic ailments such as acute rheumatic fever or rheumatoid arthritis, pulmonary ailments such as emphysema, systemic mastocytosis, psoriasis, or else other dermatological ailments such as atrophic polyctondritis, erythermalgia, or necrobiosis lipoidica. Systemic lupus erythematosus is also illustrative.

Whatever the phenomenon envisaged, all of these mechanisms exhibit a common manifestation, which is expressed by an inflammatory reaction, the terminal facet of which can be measured by the release, by the mastocytic, endothelial, keratinocyte, fibroblast, melarocytic and/or Langerhans cells of the skin, of at least one inflammation mediator such as histamine, serotonin, heparin, leukotrienes, prostaglandins, cytokines, nitrogen monoxide or reactive oxygen species.

In particular, it is known to this art that, in response to a proinflammatory signal (chemokines and cytokines such as interleukin I), the keratinocytes in the superficial layers of the skin release interleukin 8, which contributes to the triggering of the inflammatory response.

The pharmaceutical industry has long sought to develop active agents effective for treating inflammation. Vast numbers of such active agents are known to this art and are described under the designations steroidal anti-inflammatory drugs and non-steroidal anti-inflammatory drugs (SAID and NSAID); compare, for example, the text by Schorderet and Dayer "Pharmacologie. Des concepts fondamentaux aux applications thérapeutiques" (Pharmacology. Concepts which are fundamental to therapeutic applications), 1992, chapter 37, pages 541–561. 2nd Edition, Frison-Roche/Slatkine editors.

Aside from the fact that the known anti-inflammatory agents often exhibit not inconsiderable side effects, serious need continues to exist for novel compounds/formulations eliciting anti-inflammatory activity, in particular for minor skin disorders/afflictions such as, for example, sensitive skins, skin discomfort, skin stretching, skin itching, skin swelling, skin pain, skin flushing, heat sensation of the skin, erythemas, in particular due to ultraviolet rays, and pruritus.

SUMMARY OF THE INVENTION

Accordingly, a major object of the present invention is the provision of novel anti-inflammatory active agents which are conspicuously devoid of substantial adverse side effects.

Briefly, the present invention features novel anti-inflammatory compositions comprising, as the active principle therein, an effective amount of at least one peptide derivative of α-type melanocyte stimulating hormone (α-MSH), or any functional biological equivalent thereof, formulated together with at least one algal extract of marine origin.

DETAILED DESCRIPTION OF BEST MODE AND SPECIFIC/PREFERRED EMBODIMENTS OF THE INVENTION

More particularly according to the present invention, the peptide derivative is a derivative of α-type melanocyte stimulating hormone (α-MSH) or melanotropin. While α-MSH was originally described as being produced by the pituitary gland, the brain in general, the blood, the skin and other tissues are also able to produce α-MSH.

Thus, it has been shown by Schauer et al. (*J. Clin. Invest.*, 93, May 1994 pp. 2258–2262) that the keratinocytes of the epidermis are a source of α-MSH. Receptors for α-MSH are present in a large number of cell types, in particular in the hair follicles of the human scalp (*Pigment Cell Res.*, 4:193–8, 1991).

(1–13) α-MSH is known for its antipyretic activity, its anti-inflammatory activity and its pigmentation-promoting activity. This neuropeptide is recognized for inhibiting the inflammation which is induced by cytokines and other inflammation mediators, as well as by irritants.

The antipyretic signal of α-MSH is situated at its carboxy terminal sequence and can be mimicked by the 11–13 carboxy terminal tripeptide (L)Lys(L)Pro(L)Val (Watanabe et al., *Brain Research Bulletin.*, Vol. 32. pp. 311–314, 1993).

Thus, U.S. Pat. No. 5,028,592 and WO-88/00833 describe the use of the tripeptide (L or D)Lys-(L)Pro-(L or D)Val in an anti-inflammatory therapeutic treatment and the preparation of such a drug for treating inflammation.

Other derivatives of α-MSH are recognized for their anti-inflammatory activity. For example, WO-95/08564, hereby expressly incorporated by reference, describes the anti-inflammatory activity of compounds which comprise at least one 4-amino acid sequence from α-MSH conjugated to thioctic acid.

The following compounds I to VII described in WO-95/08564 are more specifically representative:
I. [(DL)Lip] Glu-His-D.homoPhe-Arg-Trp-Gly-NH$_2$
II. [(DHLip] Glu-His-D.homoPhe-Arg-Trp-Gly-NH$_2$
III.[(DL)Lip] Glu-His-ParaFluoroPhe-Arg-Trp-Gly-NH$_2$
IV. [(DL)Lip] His-D.homoPhe-Arg-Trp-NH$_2$
V. [N.lipoyl-Lysine] Glu-His-D.homoPhe-Arg-Trp-Gly-NH$_2$
VI. [N.lipoyl-Lysine] His-D.homoPhe-Arg-Trp-Gly-NH$_2$
VII.[N.lipoyl-Lysine] His-D.homoPhe-Arg-Trp-NH$_2$
as well as the derivatives thereof, in particular the salts, esters or amides.

It should be appreciated that SEPORGA markets a product under the trademark MODULENE® which is a peptide derivative of α-MSH and which exhibits anti-inflammatory properties.

Nonetheless, it has now surprisingly and unexpectedly been determined that the anti-inflammatory properties of derivatives of α-MSH can be markedly enhanced by formulating these derivatives in combinatory immixture with an algal extract of marine origin.

Thus, it has now been demonstrated that intimately admixing a peptide derivative of α-MSH with an algal extract of marine origin exhibits an anti-inflammatory effect which is greater than the simple addition of the anti-inflammatory effects which these active agents exhibit when administered individually. Furthermore, it too has been demonstrated that the immixture elicits an anti-inflammatory response, while each of the constituents of the subject compositions, at concentrations at which, when administered alone, no therapeutic activity is observed.

Thus, other than the advantage that the combinatory formulation exhibits an anti-inflammatory response which is greater than that of the active agents considered individually, the immixture also makes it possible to incorporate each of the components thereof at concentrations which are lower than those required for each of the active agents when administered alone.

The examples presented below illustrate these particular features.

Accordingly, this invention features anti-inflammatory compositions which comprise, as the active principles thereof, an effective amount of at least one peptide derivative of α-MSH, or any functional biological equivalent, and at least one algal extract of marine origin.

By "functional biological equivalent" is intended a peptide which is functionally equivalent in terms of biological function and at least one of whose amino acid residues has been exchanged for an amino acid residue having a similar hydropathic index.

The hydropathic index is an index which is assigned to amino acids in accordance with their hydrophobicity and their charge (Kyte et al., *J. Mol. Biol.*, 157:105 (1982)).

Among amino acids, the geometry of these molecules is such that they can theoretically appear in the form of different optical isomers. Thus, there is a molecular conformation of the amino acid (aa) which is such that it turns the plane of polarization of light to the right (dextrorotatory conformation or D-aa) and a molecular conformation of the amino acid (aa) which is such that it turns the plane of polarization of light to the left (laevorotatory conformation or L-aa).

Nature has maintained only the laevorotatory conformation for the natural amino acids. Consequently, if the peptide employed in the compositions according to the invention is of natural origin, this peptide will comprehend amino acids of the L-aa type. However, chemical synthesis in the laboratory makes it possible to prepare amino acids possessing the two possible conformations. Proceeding from this base material, it is possible to incorporate amino acids in the form of dextrorotatory or laevorotatory optical isomers equally well during the peptide synthesis. It is thus possible, during the peptide synthesis, to incorporate the amino acid residues Lysine-Proline-Valine equally well in their D-Lysine (D-Lys), L-Lysine (L-Lys), D-Proline (D-Pro), L-Proline (L-Pro), D-Valine (D-Val) or L-Valine (L-Val) form.

Hence, the peptide derivatives of the invention can be peptides whose amino acid residues are equally well in the form of dextrorotatory or laevorotatory optical isomers.

The peptides containing at least one of the following tripeptides are exemplary:
D-Lys-D-Pro-D-Val,
D-Lys-D-Pro-L-Val,
D-Lys-L-Pro-D-Val,
L-Lys-D-Pro-D-Val,
D-Lys-L-Pro-L-Val,
L-Lys-D-Pro-L-Val,
L-Lys-L-Pro-D-Val,
L-Lys-L-Pro-L-Val.

It will of course be appreciated that, consistent herewith, it is possible to formulate more than one peptide. In this event, the peptide mixture can be one of the possible combinations of the peptides indicated above.

It could transpire that, for reasons of resistance to degradation, according to the invention, a protected form of the peptide is required. The form of the protective group should obviously be a form which is biologically compatible. A large number of biologically compatible protective groups are available, such as, for example, acylation or acetylation of the amino terminal endgroup and/or amidation of the carboxy terminal endgroup.

Thus, the peptides of the invention can be peptides which are or are not in protected form.

Preferred protective groups are those based on acylation or acetylation of the amino terminal and/or on amidation of the carboxy terminal endgroup.

In particular according to the invention, the peptide derivative of α-MSH is selected from among the peptide derivatives comprising at least the tripeptide Lys-Pro-Val, the peptide derivatives comprising at least one 4-amino acid sequence from α-MSH which is or is not conjugated to thioctic acid, and, more preferably, the compounds described in WO-95/08564.

Preferred are the following compounds I to VII:
I [(DL)Lip] Glu-His-D.homoPhe-Arg-Trp-Gly-NH$_2$
II [(DH Lip] Glu-His-D.homoPhe-Arg-Trp-Gly-NH$_2$
III [(DL)Lip] Glu-His-ParaFluoroPhe-Arg-Trp-Gly-NH$_2$
IV [(DL)Lip] His-D.homoPhe-Arg-Trp-NH$_2$
V [N.lipoyl-Lysine] Glu-His-D.homoPhe-Arg-Trp-Gly-NH$_2$
VI [N.lipoyl-Lysine] His-D.homoPhe-Arg-Trp-Gly-NH$_2$
VII [N.lipoyl-Lysine] His-D.homoPhe-Arg-Trp-NH$_2$
as well as the derivatives of these molecules, e.g., the salts, esters or amides thereof.

A peptide derivative comprising at least the tripeptide Lys-Pro-Val and which is preferred according to this invention is the tripeptide Lys-Pro-Val itself and, more particularly, the tripeptide Lys-Pro-Val in which at least the Proline amino acid residue is in the unnatural dextrorotatory conformation (DPro residue).

Another derivative which is preferred according to this invention is the derivative marketed by Seporga under trademark Modulene®.

The peptide in accordance with the invention can, of course, be of natural origin. This implies that it can have been purified from natural biological material. It is possible, in this regard, to note, by way of example, α-MSH, which is widely present in the central nervous system and which can, inter alia, be purified from pituitary glands. However, given the current progress in chemical genetics, it is now quite easy to synthesize peptides, even of substantial length, to order.

Thus, the peptide derivatives of the invention can be peptides of natural or synthetic origin.

In the compositions of the invention, the peptide derivative can be a mixture of peptide derivatives.

The algal extract of marine origin can be any algal extract of marine origin, whatever the process by which it is obtained, with the reservation that it corresponds to the criterion selected for the invention, namely, that of exerting an anti-inflammatory enhancing effect on the anti-inflammatory activity of the peptide derivative.

Preferably, the algal extract of marine origin is an extract of brown algae of the Laminaria family. Even more preferably, the brown alga is an alga of the species *Laminaria digitata*.

An extract which is particularly preferred is an oligosaccharide solution which is obtained by enzymic depolymerization of brown algal membrane polysaccharides, such as described, in particular, in FR-2,753,628, hereby expressly incorporated by reference.

In this respect, an algal extract of marine origin which is particularly preferred according to the invention is an extract marketed by CODIF INTERNATIONAL under the designation PHYCOSACCHARIDES ANTI-IMNFLAMMATION® and which is a concentrated solution of an oligosaccharide which is obtained by the controlled enzymic depolymerization of membrane polysaccharides of a brown alga. It comprises the sequence of two uric acids: mannuronic acid and guluronic acid.

The compositions of the invention are of course compositions which are destined for cosmetic or pharmaceutical application.

The amount of each of the components of the admixture in accordance with the invention depends, quite obviously, on the desired effect and should be an amount which is effective for ensuring that the mixture elicits the desired effect, in particular an anti-inflammatory response.

To provide an order of magnitude the compositions of the invention advantageously comprise the peptide derivative in an amount by weight which represents from $10^{-6}\%$ to 10% of the total weight of the composition, and preferably in an amount which represents from $10^{-3}\%$ to 5% of the total weight of the composition.

Similarly, also to provide an order of magnitude, the compositions of the invention advantageously comprise the algal extract in an amount by weight which represents from 0.01% to 10% of the total weight of the composition, and preferably in an amount which represents from 0.02% to 5% of the total weight of the composition.

The invention also features formulating, as the active principle, of immixture of an effective amount of at least one peptide derivative of α-MSH, or any functional biological equivalent thereof, with at least one algal extract of marine origin into compositions well suited for treating inflammation.

This invention also features formulating, as the active principle, of immixture of an effective amount of at least one peptide derivative of α-MSH, or any functional biological equivalent thereof, with at least one algal extract of marine origin into compositions well suited for partially or totally inhibiting the production of interleukin 8, in particular by the keratinocytes of the skin.

Examples of disorders which manifest an inflammatory component are those indicated above.

Such inflammatory disorders may be skin disorders or systemic disorders.

Thus, the compositions comprising at least one peptide derivative of α-MSH and at least one algal extract of marine origin according to the invention are well suited for controlling disorders which manifest an inflammatory component, more specifically skin disorders.

In particular, the compositions according to the invention are useful for controlling skin ailments and afflictions such as sensitive skins, skin discomfort, skin stretching, skin itching, skin swelling, skin pain, skin flushing, heat sensation of the skin, erythemas, especially those due to ultraviolet rays, pruritus, erythema nodosum, urticaria, insect bites, allergies and alopecia in its inflammatory phases.

Even more particularly, the compositions according to the invention are useful for controlling skin irritations and/or sores and/or dysaesthesic sensations and/or heating sensations and/or pruritus of the skin and/or the mucous membranes.

Whatever the embodiment of the invention, the subject compositions can be ingested, injected or topically applied to the skin (on any region of the skin of the body), the hair, the nails or the mucous membranes (oral, jugal, gingival, genital and conjunctival). Depending on the mode of administration, the compositions according to the invention can be formulated into any of the galenic forms which are conventional in this art, e.g., formulated into any suitable medium, whether carrier, diluent or vehicle therefor.

For topical application onto the skin, the subject compositions can have the form, in particular, of an aqueous or oily solution or of a dispersion of the lotion or solution type, of emulsions of liquid or semi-liquid consistency of the milk type, which are obtained by dispersing a fatty phase in an aqueous phase (O/W) or vice versa (W/O), or of suspensions or emulsions of soft consistency of the aqueous or anhydrous cream or gel type, or else of microcapsules or microparticles or of vesicular dispersions of the ionic and/or non-ionic type. These compositions are formulated in accordance with the usual techniques. They can also be employed for the hair in the form of aqueous, alcoholic or hydroalcoholic solutions, or in the form of creams, gels, ointments, emulsions or mousses, or else in the form of aerosol compositions which also comprise a propellant under pressure.

For injection, the compositions can be in the form of an aqueous or oily lotion or in the form of a solution. For the eyes, the compositions are advantageously in the form of drops and, for ingestion, in the form of capsules, granules, syrups or tablets.

The amounts of the different constituents of the compositions according to the invention are those which are normally employed in the fields under consideration.

These compositions constitute, in particular, cleansing creams, protection creams, treatment creams or care creams for the face, for the hands, for the feet, for the large anatomical folds or for the body (for example, day creams, night creams, makeup removing creams, foundation creams and sunscreen creams), foundation liquids, makeup removing milks, body milks for protection or care, after-sun milks, lotions, gels or mousses for the care of the skin, such as cleansing lotions, sunscreen lotions, lotions for artificial tanning, bath compositions, deodorant compositions which comprise a bactericidal agent, after-shave gels or lotions, depilatory creams, compositions for treating insect bites, pain-relief compositions, and compositions for treating certain disorders of the skin such as eczema, rosacea, psoriasis, lichens and severe pruritures.

The compositions according to the invention can also be formulated as solid preparations constituting soaps or cleansing bars.

The subject compositions can also be packaged in the form of an aerosol composition which also comprises a propellant under pressure.

The compositions according to the invention can also be formulated for hair care, in particular a shampoo, a hair-setting lotion, a treatment lotion, a hair-styling cream or gel, a dye composition (in particular oxidation dyes), where appropriate in the form of coloring shampoos, restructuring lotions for the hair, a permanent-waving composition (in particular a composition for the initial stage of a permanent-waving operation), a lotion or gel preventing hair loss, an antiparasitic shampoo, etc.

The subject compositions are also useful for oral/dental application, for example formulated as a toothpaste. In this case, the compositions can contain adjuvants and additives which are customary for compositions for oral use, in particular surface-active agents, thickening agents, moistening agents, polishing agents such as silica, various active ingredients such as fluorides, in particular sodium fluoride, and, where appropriate, sweeteners such as sodium saccharinate.

When the composition is an emulsion, the proportion of the fatty phase advantageously ranges from 5% to 80% by weight, preferably from 5% to 50% by weight, the total weight of the composition. The oils, the waxes, the emulsifiers and the coemulsifiers employed in the compositions in emulsion form are selected from those which are customary in the cosmetic field. The emulsifier and the coemulsifier are advantageously present in the composition in a proportion ranging from 0.3% to 30% by weight, preferably from 0.5% to 20% by weight, of the total weight of the composition. The emulsion may furthermore contain lipid vesicles.

When the composition is an oily solution or gel, the fatty phase can represent more than 90% of the total weight of the composition.

In known manner, the cosmetic compositions may also contain additives and adjuvants which are customary in the cosmetic field, such as hydrophilic or liporhilic gelatinizing agents, hydrophilic or lipophilic active agents, preservatives, antioxidants, solvents, perfumes, fillers, filters, sequestering agents, odor absorbents and dyes and colorants. The amounts of these different additives and adjuvants are those which are normal in the cosmetic field, for example from 0.01% to 10% of the total weight of the composition. Depending on their nature, these additives and adjuvants can be introduced into the fatty phase, into the aqueous phase and/or into the lipid spherules. Exemplary oils or waxes which are useful according to the invention, include mineral oils (liquid paraffin), vegetable oils (liquid fraction of karite butter, sunflower oil), animal oils (perhydrosqualene), synthetic oils (Purcellin's oil), siliconated oils or waxes (cyclomethicone) and fluorinated oils (perfluoropolyethers), beeswax and carnauba wax, or paraffin. Fatty alcohols and fatty acids (stearic acid) can be added to these oils.

Exemplary emulsifiers which are useful according to the invention include glycerol stearate, polysorbate 60, and the mixture of PEG-6/PEG-32/glycol stearate which is marketed by Gattefosse under the trademark Tefose R 63.

Exemplary solvents according to the invention include lower alcohols, in particular ethanol, isopropanol and propylene glycol.

And exemplary hydrophilic gelatinizing agents according to the invention include carboxyvinyl polymers (carbomer), acrylic copolymers such as acrylate/alkyl acrylate copolymers, polyacrylamides, polysaccharides such as hydroxypropylcellulose, natural gums and clays, and lipophilic gelatinizing agents include are modified clays such as bentones, metallic salts of fatty acids such as aluminum stearates, and hydrophobic silica, ethylcellulose and polyethylene.

The subject compositions can contain other hydrophilic active compounds such as proteins or protein hydrolysates, amino acids, polyols, urea, allantoin, sugars and sugar derivatives, water-soluble vitamins, plant extracts and hydroxy acids.

Exemplary lipophilic active compounds include retinol (vitamin A) and derivatives thereof, tocopherol (vitamin E) and derivatives thereof, essential fatty acids, ceramides, essential oils, and salicylic acid and derivatives thereof.

The present invention also features a cosmetic treatment regime or regimen, in particular with a view to decreasing inflammation, which treatment is characterized in that a composition as described above is topically applied to the skin, to the hair and/or to the mucous membranes.

Too, this invention features, in particular, a cosmetic treatment with a view to achieving a soothing effect on the skin, characterized in that a composition as described above is topically applied to the skin, to the hair and/or to the mucous membranes.

The cosmetic treatments of the invention can be implemented, in particular, by topically applying the hygienic or cosmetic compositions as described above in accordance with the utilization technique which is customary for these compositions. For example: application of creams, gels, solutions, lotions, makeup removing milks or sunscreen compositions or after-sun compositions to the dry skin or the dry hair, application of a hair lotion to wet hair, of shampoos, or else application of dentifrice to the gums.

In order to further illustrate the present invention and the advantages thereof, the following specific examples are given, it being understood that same are intended only as illustrative and in nowise limitative.

In said examples to follow, all parts and percentages are given by weight, unless otherwise indicated.

EXAMPLE 1

Assay of Interleukin 8 which was Induced by Interleukin 1 in the Supernatant from DK7 Cells Principle and objective of the experiment:

This test permitted the anti-inflammatory potential of various molecules to be assessed on a keratinocyte cell line (DK7). In this test, an inflammatory response was mimicked by increasing the production of IL-8 by the DK7 cells by adding IL-1α to the culture medium. The effect of a molecule was then measured by its inhibitory action with regard to this increased production.

Origin of the Cells

Non-neoplastic immortalized (infected with SV40-T-Ag +human papilloma virus 16 E6/E7) human cells, which are designated DK7-Nestlé Recherche cells and which are described in PCT/EP-96/05812 (Société des produits Nestlé).

Procedure:

DK7 cells, which were stored in frozen form, were first cultured in accordance with standard protocols in a 75 cm$^2$ flask, previously coated with a coating solution (5 mg of human fibronectin (Sigma)+5 ml of vitrogen 100 (bovine collagen which had been purified for cell culture/PC0701/ collagen corporation)+50 ml of a 0.1% solution of BSA (BSA/ref: 343020/biofluids)+440 ml of NR1 medium), in the presence of 20 ml of NR2 medium (taking 500 ml of NR1-based serum-free medium (biofluids No. P185-500), add 2.5 ml of bovine pituitary extract (BPE) (biofluids No. 210) and 5 ml of antibiotic/antimycotic (ref: 15240-C39/ GIBCO)). The cells were then cultured through to confluence.

The cells were then detached from the flask by trypsinization using standard techniques. On D=0, the cells are seeded in (a) precoated 96-well plate(s) at the rate of 200 μl of medium per well (cell density: 6.10$^4$ cell/ml).

On D=1, the cells were contacted with the product to be tested. 30 to 50 minutes after the treatment, IL-1 was added to the culture medium in a concentration of 2.5 ng/ml. The cells were then incubated at 37° C. for 24 hours. The assay of IL-8 in the supernatants, as well as a protein assay, preceded by an XTT/BrdU test, were then performed.

IL-8 assay:

This assay was carried out using an ELISA/IL-8 kit (code RPN 2764/Biotrak/Amersham) in accordance with the information provided by the supplier.

The assay was performed on a 50 μl volume of culture medium.

The optical density was read at 450 nm using a "Labsystems Multiscan Multisoft" spectrophotometer.

Protein assay:

A protein assay was carried out on each sample using a protein assay kit (BCA protein assay kit/ref.: 23225/Pierce), which was stored at room temperature.

Products tested:

DM1=1 μM MODULENE®:
DM10=10 μM MODULENE®:
Phyco=50 μM PHYCOSACCHARIDES ANTI-INFLAMMATION®
DM1+Phyco=1 μM MODULENE®=50 μM PHYCOSACCHARIDES ANTI-INFLAMMATION®
DM10+Phyco=10 μM MODULENE®=50 μM PHYCOSACCHARIDES ANTI-INFLAMMATION®

Control: Cells which had been treated with IL-1 and not treated with any of the compounds to be tested.

Results:

The IL-8 assay data below are expressed in pg of IL-8 per μg of protein:

|  | IL-8 | % inhibition |
|---|---|---|
| Control | 44.04 | — |
| DM1 + Phyco | 24.73 | 43.8 |
| DM10 + Phyco | 22.71 | 48.4 |
| DM1 | 43.69 | 0.8 |
| DM10 | 34.89 | 20.8 |
| Phyco | 52.95 | 0 |

The combination DM+phyco inhibited significantly the production of IL-8 which was produced in the control batch.

The combination DM1+Phyco inhibited the production of IL-8, whereas DM1 alone had no effect on IL-8. This result demonstrated the synergistic effect of the MODULENE®+ PHYCOSACCHARIDES ANTI-INFLAMMATION® combination.

EXAMPLE 2

The following specific compositions according to the present invention were formulated simply by intimately admixing the several components thereof.

Composition 1: Day Cream

| Phycosaccharide anti-inflammation ®* | 5.00% |
|---|---|
| Modulene ®** | 1.00% |
| Sucrose stearate | 4.00% |
| Stearyl alcohol | 2.00% |
| Cyclohexasiloxane | 9.00% |
| Mineral oil | 4.00% |
| Glycerol | 5.00% |
| Xanthan gum | 0.30% |
| Carbomer | 0.50% |
| Preservatives | 0.30% |
| Perfume | 0.30% |
| Water | qs for 100 |

Composition 2: Care Liquid

| Phycosaccharide anti-inflammation ®* | 1.00% |
|---|---|
| Modulene ®** | 1.00% |
| Stearyl alcohol | 0.40% |
| Sorbitan stearate | 1.50% |
| Glycerol | 5.00% |
| Xanthan gum | 0.20% |
| Carbomer | 0.10% |
| Cyclohexasiloxane | 7.00% |
| Preservatives | 0.30% |
| Perfume | 0.20% |
| Water | qs for 100 |

Composition 3: Lotion

| Phycosaccharide anti-inflammation ®* | 0.02% |
|---|---|
| Modulene ®** | 1.00% |
| Propylene glycol | 2.00% |
| Cornflower extract | 0.10% |
| Preservatives | 0.10% |
| PEG 60 hydrogenated castor oil | 0.40% |

| | |
|---|---|
| Perfume | 0.10% |
| Water | qs for 100 |

Phycosaccharide anti-inflammation®*: 5% Laminaria digitata-derived oligosaccharide (MW 3500 daltons) in water Modulene®**: (1%) dextran-stabilized lipoylpeptide in stabilized aqueous solution (0.3% Phenonip)

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. An anti-inflammatory composition comprising an immixture of (1) at least one peptide derivative of α-type melanocyte stimulating hormone (α-MSH), and (2) at least one oligosaccharide solution obtained by enzymatic depolymerization of brown algal membrane polysaccharides.

2. The anti-inflammatory composition of claim 1, further comprising a therapeutically acceptable vehicle, diluent or carrier therefor.

3. The anti-inflammatory composition as defined by claim 1, which comprises at least one peptide derivative of α-MSH, said at least one peptide derivative comprising the tripeptide Lys-Pro-Val.

4. The anti-inflammatory composition as defined by claim 1, which comprises at least one peptide derivative of α-MSH, said at least one peptide derivative comprising at least one 4-amino acid sequence from α-MSH conjugated to thioctic acid.

5. The anti-inflammatory composition as defined by claim 3, wherein said tripeptide Lys-Pro-Val, at least the amino acid residue Pro is in the dextrorotatory conformation.

6. The anti-inflammatory composition as defined by claim 1, comprising an extract of brown algae of the Laminaria genus.

7. The anti-inflammatory composition as defined by claim 6, comprising an extract of brown algae of the species *Laminaria digitata*.

8. The anti-inflammatory composition as defined by claim 1, comprising from $10^{-6}\%$ to 10% by weight of said at least one peptide derivative of α-MSH.

9. The anti-inflammatory composition as defined by claim 8, comprising from $10^{-3}\%$ to 5% by weight of said at least one peptide derivative of α-MSH.

10. The anti-inflammatory composition as defined by claim 8, comprising from 0.01% to 10% by weight of said at least one brown algal membrane polysaccharide.

11. The anti-inflammatory composition as defined by claim 9, comprising from 0.02% to 5% by weight of said at least one brown algal membrane polysaccharide.

12. The anti-inflammatory composition of claim 1, further comprising an aqueous solution, an oily solution, a dispersion, an emulsion, a milk, a suspension, a cream, a gel, a lotion, an ointment, a syrup, a mousse, a spray, a vesicular dispersion, microcapsules or microparticles.

13. The anti-inflammatory composition of claim 2, wherein the vehicle is selected from the group consisting of capsules, granules and tablets.

14. The anti-inflammatory composition of claim 1, further comprising a composition selected from the group consisting of a shampoo, a hair-styling formulation, a permanent-waving composition, and a hair-restructuring lotion.

15. The anti-inflammatory composition of claim 1, further comprising a toothpaste.

16. The anti-inflammatory composition of claim 1, further comprising a hydrophilic gelatinizing agent, a lipophilic gelatinizing agent, a hydrophilic active agent, a lipophilic active agent, a preservative, an antioxidant, a solvent, a perfume, a filler, a sequestering agent, an odor absorber, a dye, a colorant, or a mixture thereof.

17. The anti-inflammatory composition of claim 1, wherein the composition comprises at least one peptide derivative of α-MSH, or the salt, ester or amide thereof, selected from the group consisting of (DL-Lip) Glu-His-D-homoPhe-Arg-Trp-Gly-NH$_2$, (DH-Lip) Glu-His-D-homoPhe-Arg-Trp-Gly-NH$_2$, (DL-Lip) Glu-His-ParaFluoroPhe-Arg-Trp-Gly-NH$_2$, (DL-Lip) His-D-homoPhe-Arg-Trp-NH$_4$, (N-lipoyl-Lysine) Glu-His-D-homoPhe-Arg-Trp-Gly-NH$_2$, (N-lipoyl-Lysine) His-D-homoPhe-Arg-Trp-Gly-NH$_2$, and (N-lipoyl-Lysine) His-D-homoPhe-Arg-Trp-NH$_2$, wherein Lip is thioctic acid.

18. The anti-inflammatory composition of claim 1, further comprising a cosmetically acceptable vehicle, diluent or carrier therefor.

19. The anti-inflammatory composition of claim 1, further comprising a soap or cleansing bar.

* * * * *

SEQUENCE LISTING

```
<160> NUMBER OF SEQ ID NOS: 4

<210> SEQ ID NO 1
<211> LENGTH: 6
<212> TYPE: PRT
<213> ORGANISM: Artificial Sequence
<220> FEATURE:
<221> NAME/KEY: PEPTIDE
<222> LOCATION: (3)
<223> OTHER INFORMATION: Amino acid 3 is xaa wherein xaa = D.homoPhe.
<220> FEATURE:
<223> OTHER INFORMATION: Description of Artificial Sequence: anti-
      inflammatory activity from alpha-MSH conjugated to thioctic acid.

<400> SEQUENCE: 1

Glu His Xaa Arg Trp Gly
  1               5

<210> SEQ ID NO 2
<211> LENGTH: 6
<212> TYPE: PRT
<213> ORGANISM: Artificial Sequence
<220> FEATURE:
<221> NAME/KEY: PEPTIDE
<222> LOCATION: (3)
<223> OTHER INFORMATION: Amino acid 3 is xaa wherein xaa =
      ParaFluoroPhe.
<220> FEATURE:
<223> OTHER INFORMATION: Description of Artificial Sequence:anti-
      inflammatory activity from alpha-MSH conjugated to thioctic acid.

<400> SEQUENCE: 2

Glu His Xaa Arg Trp Gly
  1               5

<210> SEQ ID NO 3
<211> LENGTH: 4
<212> TYPE: PRT
<213> ORGANISM: Artificial Sequence
<220> FEATURE:
<221> NAME/KEY: PEPTIDE
<222> LOCATION: (2)
<223> OTHER INFORMATION: Amino acid 2 is xaa wherein xaa = D.homoPe.
<220> FEATURE:
<223> OTHER INFORMATION: Description of Artificial Sequence:anti-
      inflammatory activity from alpha-MSH conjugated to thioctic acid.

<400> SEQUENCE: 3

His Xaa Arg Trp
  1

<210> SEQ ID NO 4
<211> LENGTH: 5
<212> TYPE: PRT
<213> ORGANISM: Artificial Sequence
<220> FEATURE:
```

```
<221> NAME/KEY: PEPTIDE
<222> LOCATION: (2)
<223> OTHER INFORMATION: Amino acid 2 is xaa wherein xaa = D.homoPhe.
<220> FEATURE:
<223> OTHER INFORMATION: Description of Artificial Sequence:anti-
      inflammatory activity from alpha-MSH conjugated to thioctic acid.

<400> SEQUENCE: 4

His Xaa Arg Trp Gly
 1               5
```